(12) United States Patent
Walach et al.

(10) Patent No.: US 12,014,489 B2
(45) Date of Patent: Jun. 18, 2024

(54) SYSTEM FOR DETERMINING THE PRESENCE OF FEATURES IN A DATASET

(71) Applicant: AIDOC Medical LTD, Tel Aviv (IL)

(72) Inventors: Eugeniusz Walach, Haifa (IL); Elad Walach, Hallendale Beach, FL (US); Idan Bassukevitz, Giv'atayim (IL); Uri Goren Horesh, Modiin (IL); Michael Braginski, Rishon Letzion (IL)

(73) Assignee: AIDOC Medical Ltd., Tel Aviv (IL)

( * ) Notice: Subject to any disclaimer, the term of this patent is extended or adjusted under 35 U.S.C. 154(b) by 542 days.

(21) Appl. No.: 17/178,680

(22) Filed: Feb. 18, 2021

(65) Prior Publication Data
US 2022/0261985 A1    Aug. 18, 2022

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/10081* (2013.01); *G06T 2207/20081* (2013.01)

(58) Field of Classification Search
None
See application file for complete search history.

(56) References Cited

U.S. PATENT DOCUMENTS

2020/0184252 A1*  6/2020  Syeda-Mahmood .. G06V 10/26

OTHER PUBLICATIONS

Wang, Yunzhi, et al. "A two-step convolutional neural network based computer-aided detection scheme for automatically segmenting adipose tissue volume depicting on CT images." Computer methods and programs in biomedicine 144 (2017): 97-104. (Year: 2017).*

* cited by examiner

*Primary Examiner* — Samah A Beg
(74) *Attorney, Agent, or Firm* — Ziegler IP Law Group (57) ABSTRACT

A system for determining whether a dataset including a plurality of cross-sectional images includes a predetermined feature is provided. A first AI receives a dataset including a plurality of cross-sectional images, and analyses the dataset to identify a subset of cross-sectional images of the dataset capable of including the predetermined feature A second AI model receives a first cross-sectional image from the subset, analyses the first cross-sectional image to determine whether the first cross-sectional image includes the predetermined feature, and outputs an indication of whether the first cross-sectional image includes the predetermined feature. A processor is configured to obtain the output from the second AI model, and based on the output from the second AI model indicating that the first cross-sectional image includes the pre-determined feature, determine that the dataset includes the predetermined feature.

13 Claims, 9 Drawing Sheets

SYSTEM FOR DETERMINING THE PRESENCE OF FEATURES IN A DATASET

TECHNICAL FIELD

The present disclosure relates to a system for determining the presence of features in data comprising a plurality of cross-sectional images. More particular, the present disclosure relates to systems and methods for determining the presence of features in studies, and for training artificial intelligence (AI) models to determine the presence of features in data comprising a plurality of cross-sectional images.

BACKGROUND

With explosive growth of AI applications, automated processing of medical images in particular has increased rapidly. For example, deep learning techniques are used for image classification. Such approaches are frequently applied to the analysis of three dimensional (3D) volume data, such as computed tomography (CT) or magnetic resonance imaging (MRI) studies. Usually, each study is organized in the form of a large number of horizontal cross-sectional images, forming a set of images.

It is generally seen as impractical to identify individual cross-section images from these studies to feed into AI models for analysis. For example, this would require human experts that would manually determine areas of interest in the training set. At best, this would be a laborious process. At worst it would be almost impossible (e.g. it is extremely difficult for a human expert to determine which areas of the brain are suitable for contrast agent detection in a CT scan). Instead, the entire study (e.g. the entire CT study) is fed into the system. As a result, the training process often involves large volumes of irrelevant data. For example, if a patient's lungs are CT scanned for the identification of lung nodules, the CT study often includes cross-sectional images of surrounding body parts, such as the abdomen, which are irrelevant for the task at hand.

This situation causes a number of problems. For example, during the training of the AI model, a large amount of irrelevant data (i.e. irrelevant cross-sectional images) are processed, causing deterioration in the system performance. As another example, during detection (e.g. of lung nodules in CT scans), it is necessary to analyse the entire study before any conclusion can be reached. In other words, it would not be possible to conclude that there are no lung nodules present until the entire study had been analysed. This requires a significant amount of time and resources.

SUMMARY

The aspects of the disclosed embodiments are directed to provide systems and methods that overcome problems associated with conventional systems and methods.

According to an aspect, there is provided a system for determining whether a dataset comprising a plurality of cross-sectional images includes a predetermined feature, the system comprising: a first AI model to: receive a dataset comprising a plurality of cross-sectional images as an input, analyse the dataset to identify a subset of cross-sectional images of the dataset capable of including the predetermined feature, and output the subset; a second AI model to: receive a first cross-sectional image from the subset, analyse the first cross-sectional image to determine whether the first cross-sectional image includes the predetermined feature, and output an indication of whether the first cross-sectional image includes the predetermined feature; and a processor configured to: provide the dataset as an input to the first AI model, obtain the output subset from the first AI model, provide the first cross-sectional image from the subset as an input to the second AI model, obtain the output from the second AI model, and based on the output from the second AI model indicating that the first cross-sectional image includes the pre-determined feature, determine that the dataset includes the predetermined feature.

In some embodiments, the feature comprises an object, such as a cancerous lesion.

In some embodiments, the dataset is a medical imaging study.

In some embodiments, the dataset is a computed tomography, CT, study or a magnetic resonance imaging, MRI, study.

In some embodiments, the dataset is a brain CT study, and the feature is the presence contrast agent.

In some embodiments, the subset comprises only one cross-sectional image.

In some embodiments, the subset comprises a contiguous plurality of cross-sectional images.

In some embodiments, the first AI model is configured to output at least a predetermined proportion of the cross-sectional images from the dataset in the subset.

In some embodiments, based on the output from the second AI model indicating that the first cross-sectional image does not include the pre-determined feature, the processor is configured to determine that the dataset does not include the predetermined feature.

In some embodiments, based on the output from the second AI model indicating that the first cross-sectional image does not include the pre-determined feature, the processor is configured to: provide a second cross-sectional image from the subset as an input to the second AI model, obtain an output from the second AI model for the second cross-section, and based on the output from the second AI model indicating that the second cross-sectional image includes the pre-determined feature, determine that the dataset includes the predetermined feature.

In some embodiments, based on outputs from the second AI model indicating that none of the cross-sectional images include the pre-determined feature, the processor is configured to determine that the dataset does not include the predetermined feature.

In some embodiments, the second AI model is a classification model.

According to an aspect, there is provided a computer implemented method for determining whether a dataset comprising a plurality of cross-sectional images includes a predetermined feature, the method comprising: inputting, by a processor, dataset comprising a plurality of cross-sectional images into a first AI model, analysing, by the first AI model, the plurality of cross-sectional images to identify a subset of cross-sectional images of the dataset capable of including the predetermined feature, and outputting, by the first AI model, the subset; inputting, by the processor, a first cross-sectional image from the subset into a second AI model, analysing, by the second AI model, the first cross-sectional image to determine whether the first cross-sectional image includes the predetermined feature, and outputting, by the second AI model, an indication of whether the first cross-sectional image includes the predetermined feature; and based on the output of the second AI model indicating that the first cross-sectional image includes the pre-determined feature, determining, by the processor, that the dataset includes the predetermined feature.

According to an aspect, there is provided a system for training a second AI model to determine whether cross-section image includes a predetermined feature, the system comprising: a first AI model to: receive dataset comprising a plurality of cross-sectional images as an input, analyse the dataset to identify a subset of cross-sectional images of the dataset capable of including the predetermined feature, and output the subset; a second AI model to: receive a first cross-sectional image from the subset, analyse the first cross-sectional image to determine whether the first cross-sectional image includes the predetermined feature, and output an indication of whether the first cross-sectional image includes the predetermined feature; an annotation unit to obtain an annotation indicating whether the predetermined feature is in the dataset; and a processor configured to: provide the dataset as an input to the first AI model, provide the first cross-sectional image from the subset as an input to the second AI model, and compare the output from the second AI model and the annotation, and provide the result of the comparison as feedback to the second AI model to train the second AI model to determine whether a cross-sectional image includes the predetermined feature.

In some embodiments, the processor is further configured to: provide the result of the comparison as feedback to the first AI model to train the first AI model to identify a subset of a plurality of cross-sectional images in a dataset that are capable of including the predetermined feature.

In some embodiments, the annotation indicates whether the predetermined feature is in the first cross-sectional image.

According to an aspect, there is provided a computer implemented method for training a second AI model to determine whether a cross-sectional image includes a predetermined feature, the method comprising: inputting, by a processor, dataset comprising a plurality of cross-sectional images into a first AI model, analyse the dataset to identify a subset of cross-sectional images of the dataset capable of including the predetermined feature, and outputting, by the first AI model, the subset; inputting, by the processor, a first cross-sectional image from the subset into a second AI model, analysing, by the second AI model, the first cross-sectional image to determine whether the first cross-sectional image includes the predetermined feature, and outputting, by the second AI model, an indication of whether the first cross-sectional image includes the predetermined feature; and obtaining, by an annotation unit, an annotation indicating whether the predetermined feature is in the dataset; comparing, by the processor, the output from the second AI model and the annotation; and providing, by the processor, the result of the comparison as feedback to the second AI model to train the second AI model to determine whether a cross-sectional image includes the predetermined feature.

In some embodiments, the method further comprises: providing, by the processor, the result of the comparison as feedback to the first AI model to train the first AI model to identify a subset of a plurality of cross-sectional images in a dataset that are capable of including the predetermined feature.

According to an aspect, there is provided a computer-readable medium having computer-executable instructions to cause one or more processors of a computing device to carry out the methods disclosed herein.

BRIEF DESCRIPTION OF THE DRAWINGS

Embodiments of the present disclosure will now be described, by way of example only, with reference to the accompanying drawings, in which.

DETAILED DESCRIPTION OF THE DRAWINGS

Figure 1:
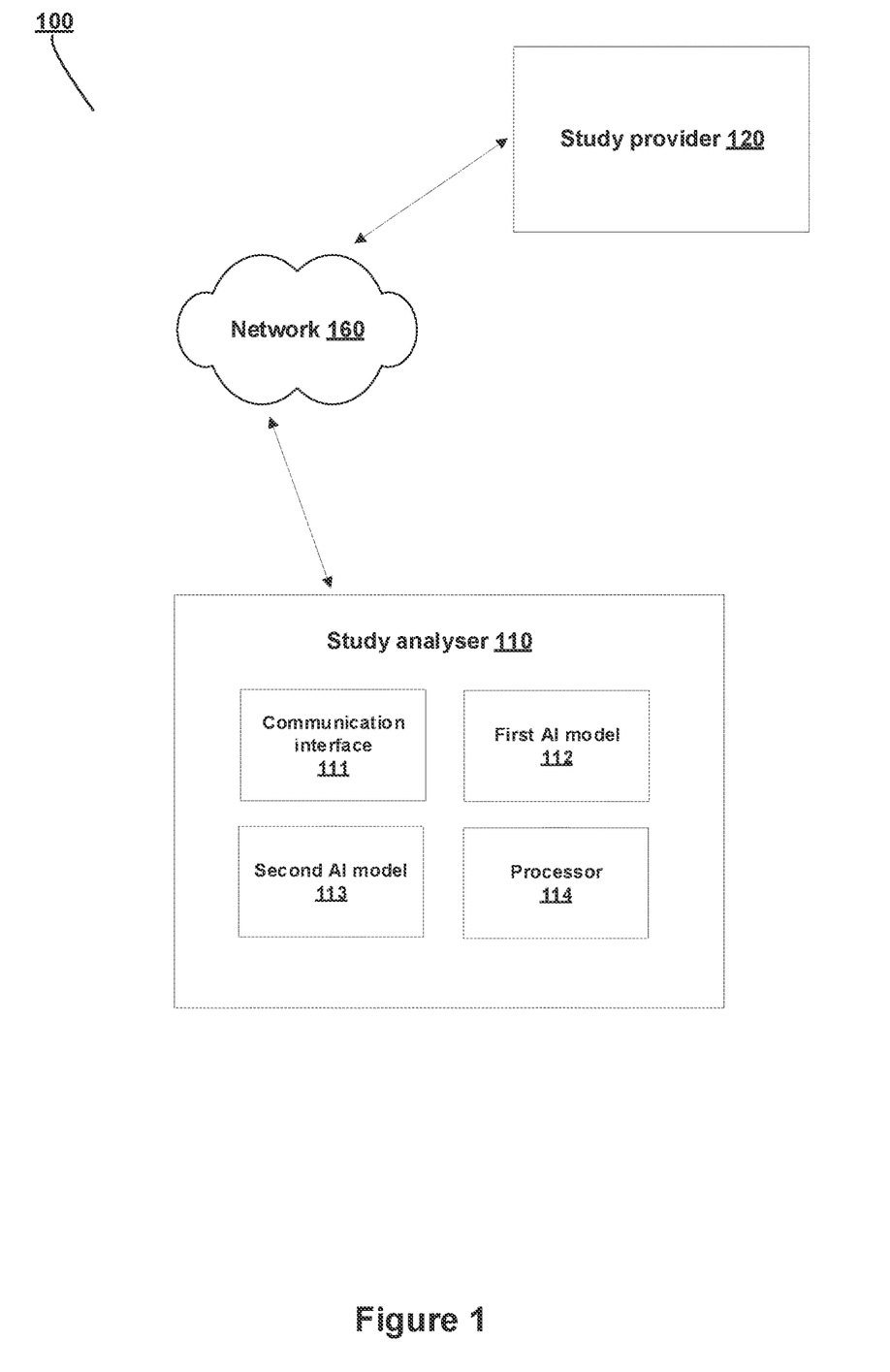
FIG. 1 shows a schematic illustration of a system according to an embodiment of the disclosed embodiments.

FIG. 1 shows a system 100 according to an embodiment. The system 100 comprises a study analyser 11, and a study provider 120. The study analyser 110 can communicate with the study provider 120 over the network 160.

It will be appreciated that in practical implementations of embodiments, there may be many such study providers and/or study analysers, but one of each will be described with relation to FIG. 1 for ease of explanation.

The network 160 in this embodiment is the internet. However, embodiments are not limited to this and any suitable communications technology could be used.

In this embodiment, the study provider 120 is configured to transmit a study to the study analyser 110 over the network. In this embodiment the study is a CT study comprising a plurality of cross-sectional images of a patient that has undergone a CT scan. However, embodiments are not limited to this and the study can be any 3D volume of a data comprising a plurality of cross-sectional images. Examples include other medical studies (e.g. MRI) as well as non-medical studies. In other words, the study is a dataset comprising a plurality of cross-sectional images. Such studies allow for the representation of 3D objects by their 2D cross-sections.

In this embodiment the study provider 120 is a server storing a plurality of CT studies. However, embodiments are not limited to this and the study provider 120 can be any device capable of transmitting a study to the study analyser 110, such as a PC, smartphone, PDA or other suitable computer device. In other embodiments, the study provider can be the device which directly obtains the study, such as a CT scanner or MRI scanner.

As shown in FIG. 1, the study analyser 110 includes a communication interface 111, a first AI model 112, a second AI model 113, and a processor 114. In this embodiment, the study analyser 110 is a single apparatus. However, embodiments are not limited to this and the study analysis functionality of other embodiments could be provided in more than one connected apparatuses (e.g. connected over the network 160).

The study analyser 111 is configured to communicate with the study provider 120 over the network 160, to receive a study. However, embodiments are not limited to this. For example, in other embodiments, the study analyser could directly obtain the study. For example, the study analyser could be a CT scanner, with the communication interface 111 directly obtaining a CT study of a patient (thereby removing the need for both the study provider 120 and the network 160).

The second AI model 113 is configured to receive a cross-sectional image as an input, to analyse the cross-sectional image (often referred to as a 'cross-section'), and to output an analysis result indicating whether or not the cross-section includes a predetermined feature. In this embodiment, the second AI model 113 acts as a classifier to classify an input cross-section as either including a lung nodule or not including a lung nodule. However, embodiments are not limited to this and the second AI model 113 in other embodiments can be configured to determine whether an input cross-section includes any predetermined feature. Furthermore, while classification is used here, embodiments are not limited to this. More generally, any suitable image analysis indicating whether a cross-section includes a predetermined feature, could be used instead. The second AI model 113 will be discussed in detail below, with reference to FIG. 2.

The first AI model 112 is configured to receive a study comprising a plurality of cross-sectional images as an input, to analyse the study, and to output an analysis result comprising a subset of the cross-sections in the study. Here, subset is used to mean at least one cross-section but, typically, not all of the cross-sections from the study.

For example, if the second AI model 113 is configured to identify lung nodules (as in this example embodiment), then the first AI model 112 filters out cross-sections that do not include lung tissue (e.g. cross-sections of the abdomen), as it would not be possible for such cross-sections to include lung nodules. As a result, the output subset of cross-sections would include only (or at least a high proportion of) cross-sections including lung tissue. However, as discussed above embodiments are not limited to the identification of lung nodules. The first AI model 112 will be discussed in detail below, with reference to FIG. 2.

In simple terms, the first AI model 112 is aimed at identifying an area of interest in the study (e.g. a plurality of cross-sections showing a lung area), while the second AI model 113 is aimed at identifying a specific feature within a single cross-section or several adjacent cross-sections (e.g. an object such as a lung nodule).

The processor 114 is configured to control operations of the study analyser 110. In this embodiment, this includes controlling the communication interface 111 to communicate with the study provider 120, controlling inputs to the second AI model 113 and first AI model 112, and performing analysis based on the outputs.

Figure 2:
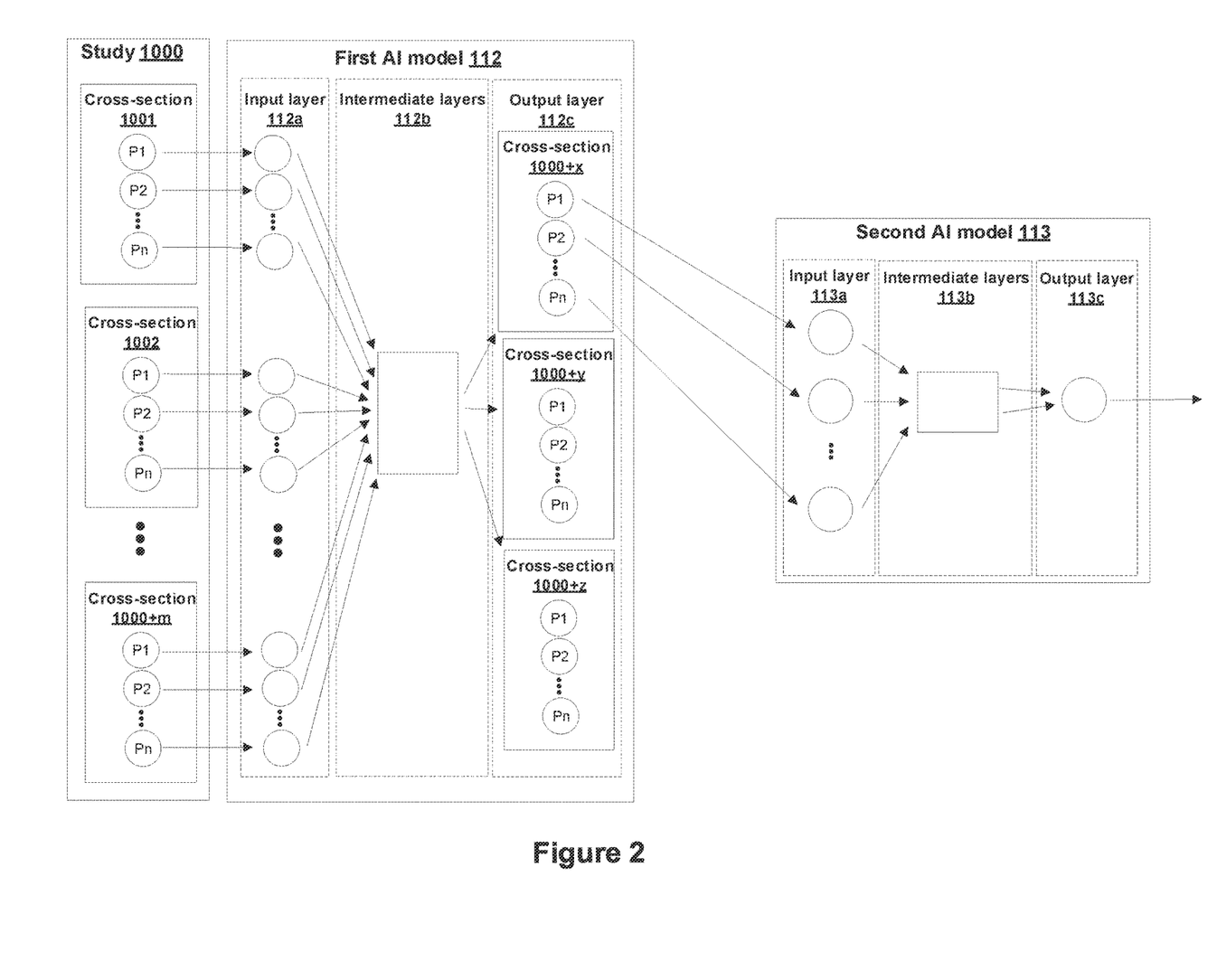
FIG. 2 shows a schematic illustration of the AI models in the system of FIG. 1.

FIG. 2 shows more detail regarding the second AI model 113 and first AI model 112, as well as a schematic view of the study 1000.

As shown in FIG. 2 the study 1000 comprises m cross-sections 1001 to 1000+m. For example, m could be 100. However, this is merely an example and m could be any suitable number (e.g. 50 or 500). Further, as shown in FIG. 2, each cross-section 1001 to 1000+m comprises a plurality of pixel values (i.e. brightness values) P1 to Pn representing each pixel in the cross-section. In this embodiment, the study 1000 is a CT study, and the pixel values are Hounsfield units. However, embodiments are not limited to this, and any suitable studies comprising cross-sections could be used instead. For example, other types of radiology study (i.e. MRI studies), or other types of study altogether (including colour images) could be used instead. Such studies could use different measurements of pixel values (e.g. pixel grayscale values instead of Hounsfield units).

In this embodiment, the number n of pixels in each cross-section 1001 to 100+m is 262,144 (i.e. 512 rows, each having 512 pixels). However, embodiments are not limited to this and cross-sections in other embodiments could have any suitable number of pixels.

In this embodiment, the first AI model 112 comprises a neural network with a deep learning architecture comprising an input layer 112a, intermediate layers 112b and an output layer 112c. The input layer 112a is configured to receive the pixel values P1 to Pn of each cross-section 1001 to 100+m in the study 1000. As mentioned above, in this embodiment the study 1000 comprises 100 cross-sections, each having 262,144 pixels. As a result, the input to the first AI model 112 comprises 26,214,400 pixel values. However, as mentioned above, embodiments are not limited to this number of cross-sections or pixels. The input layer 112a, intermediate layers 112b and output layer 112c are then configured to process the input values and to output a subset of these input values corresponding to a plurality of the input cross-sections. For example, the first AI model 112 could be configured to output half of the cross-sections.

In this embodiment (in which the ultimate aim of the study analyser 110 is to identify lung nodules), the first AI model 112 comprises a neural network that has been trained to process input studies so as to output the cross-sections including lung tissue. As the input to the first AI model 112 comprises all (or many) of the cross-sections, this allows the first AI model 112 to identify which region(s) of the study represent the lungs, based on patterns of cross-sections in the study.

Specifics regarding how the first AI model 112 is trained are provided later with reference to FIGS. 7 and 8B. While in this embodiment, the neural network is configured to identify which of the cross-sections include lung tissue, and to output those cross-sections, it will be appreciated that embodiments are not limited to this. For example, it could theoretically be the case that only specific parts of a lung can include nodules, and the first AI model 112 could be trained to output only cross-sections representing those parts of the lung.

While the intermediate layers 112b are shown as a single box in FIG. 2, it will be appreciated that this is merely for ease of illustration and that any suitable number of intermediate layers comprising any number of nodes could be used instead.

While the output layer 112c shows an example of outputting three cross-sections 1000+x, 1000+y, and 1000+z, this is merely for ease of illustration. It will be appreciated that the first AI model 112 could be configured to output any desired number of cross-sections. As mentioned above, one example is to output half of the input cross-sections. Examples on limitations of the number of output cross-sections are discussed later.

In this embodiment, the second AI model 113 comprises a neural network using a deep learning architecture comprising an input layer 113a, intermediate layers 113b and an output layer 113c. The input layer 113a is configured to receive the pixel values P1 to Pn from a single cross-section that has been output by the first AI model 112. For example, as shown in FIG. 2, the input to the input layer 113a could be the pixel values P1 to Pn of the output cross-section 100x.

As mentioned above, in this embodiment each cross-section includes 262,144 pixels. As a result, the input to the second AI model 113 comprises 262, 144 values. As discussed in detail later, in this embodiment, the second AI model 113 receives and analyses one cross-section at a time. As mentioned above, embodiments are not limited to this number of cross-sections. In other embodiments, the second AI model receives and analyses (i.e. processes) several cross-sections. As an example, in an implementation in which the second AI model is aimed at classifying lung nodules, the second AI model may consider a plurality of neighbouring cross-sections together.

In this embodiment (in which the ultimate aim of the study analyser 110 is to identify lung nodules), the second AI model 113 comprises a neural network that has been trained to process the input cross-section so as to output a classification indicating whether or not the cross-section includes a lung nodule. Specifics regarding how the second AI model 113 is trained are provider later with reference to FIGS. 6A and 6B. However, in very general terms, in this embodiment, the neural network is configured to act similarly to known image classifiers in terms of receiving an input image and outputting a classification result.

While classification is used as an example here, embodiments are not limited to this. More generally, any suitable image analysis to output a result indicating whether that image shows a predetermined feature (such as a lung nodule), could be used instead. The image classification unit 112 will be discussed below, with reference to FIG. 2.

Figure 3:
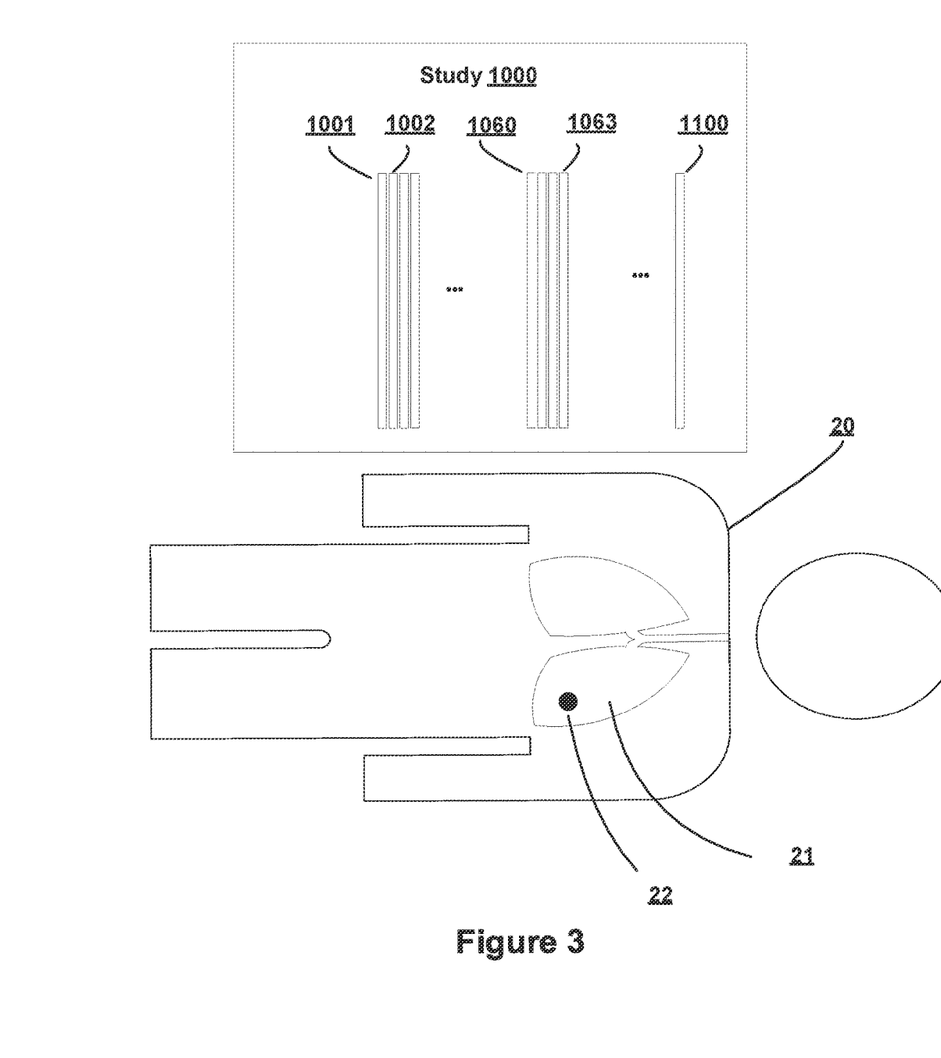
FIG. 3 shows an example correspondence between cross-sectional images and patient anatomy.

FIG. 3 shows an example correspondence between the cross-sections of the study 1000, a patient 20, the patient's lungs 21, and a nodule 22 in the lungs. As discussed above, in this embodiment the study is a lung CT study comprising 100 cross sections (but embodiments are not limited to this example).

When such CT scans are taken, the resulting CT study commonly includes not just lung tissue, but also cross-sections representing other parts of the body. In the example of FIG. 3, it can be seen that only roughly the 60th-100th cross-sections include lung tissue, and the remaining cross-sections are essentially useless for the identification of lung nodules.

Figure 4:
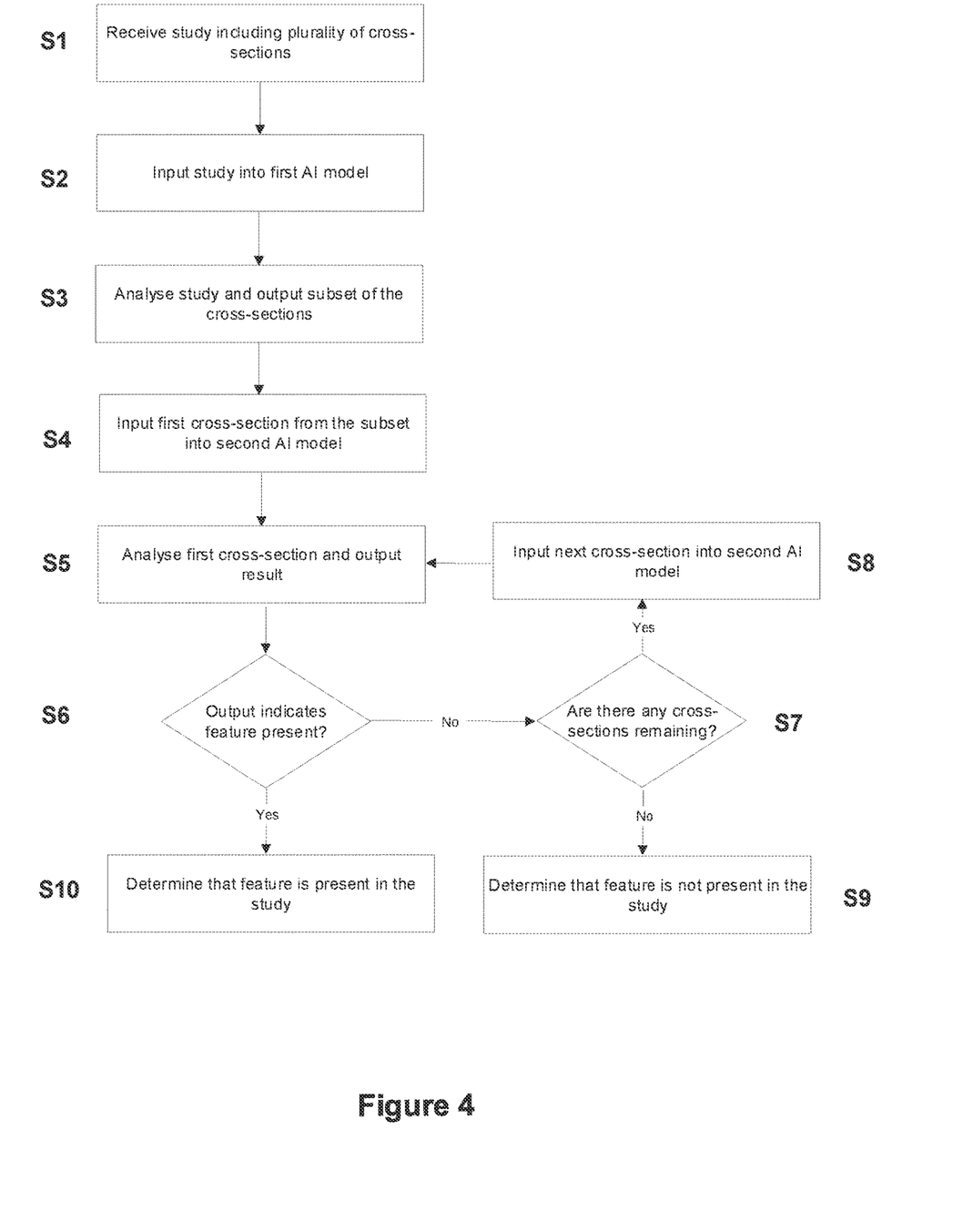
FIG. 4 shows a flowchart of the operation of the study analyser in the system of FIG. 1.
Figure 5:
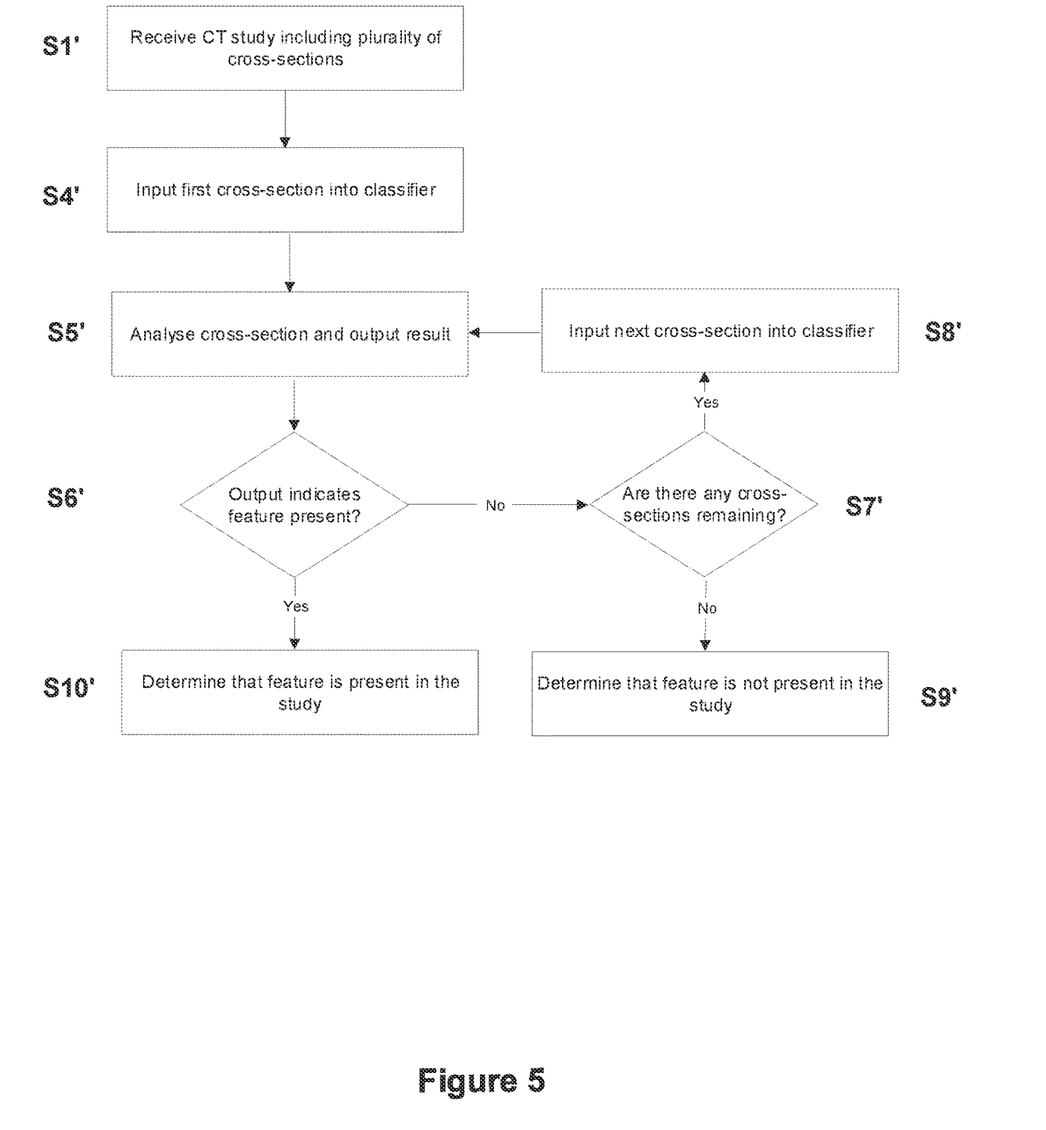
FIG. 5 shows a comparative flowchart of a study analyser that could be implemented using conventional techniques.

This example of FIG. 3 will be used for the discussions of FIGS. 4 and 5. FIG. 4 shows a flowchart of the operation of the study analyser 110, while FIG. 5 shows a comparative flowchart of a study analyser that could be implemented using conventional techniques (in particular without including a first AI model 112).

In the operation of FIG. 4, the study analyser analyses the input study 1000 to determine whether the study includes lung nodules.

At step S1, the communication interface 111 receives a study including a plurality of cross-sections 1000 to 1000+m from the study provider 120. Each cross-section comprises a plurality of pixel values P1 to Pn corresponding to a plurality of pixels of the cross-section.

In variants of this embodiment, the study analyser may instead retrieve the study from a suitable storage, receive it from a different apparatus, or directly obtain it (e.g. by performing a CT scan on a patient).

At step S2, the processor 114 inputs the study into the first AI model 112 for analysis. As discussed above with reference to FIG. 2, this involves inputting the pixels values of a plurality of cross-section in the study into the first AI model 112.

At step S3, the first AI model 112 analyses the study and outputs a subset of the cross-sections which are capable of including a lung nodule. In this example, this involves identifying cross-sections which represent (or are likely to represent) lung tissue and outputting those cross-sections, while discarding the others. However, embodiments are not limited to this. For example, in some embodiments the first AI model 112 could be trained to be more specific than this (e.g. to only output cross-sections showing a particular part of the lung). In other examples, the first AI model 112 could be trained to be less specific than this (e.g. to only output cross-sections showing body tissue, and not cross sections showing no part of the body). Specifics regarding how the first AI model 112 is trained are discussed later with reference to FIGS. 7 and 8B.

In this embodiment (i.e. when identifying cross-sections that represent lung tissue), the first AI model 112 uses a binary search. Specifically, the first AI model 112 begins by processing one cross-section of the input study (e.g. a cross-section in the middle of the study). If this cross-section shows lung tissue, the first AI model 112 then analyses a cross-section halfway between this middle cross-section and the bottom. If this also shows lung, then another cross-section closer to the bottom is processed, and so on. In this way, a bottom border of the lung can be found. The process can then be repeated to find a top border. If the first processed cross-section (i.e. the cross-section in the middle of study) does not show lung tissue, then a cross-section from a different part of the study can be processed, and further cross-sections processed to identify the borders.

In this way, the first AI model 112 only needs to process a small number of cross-sections in the study in order to identify the cross-sections representing lung tissue, thereby reducing the time needed to process the study compared to a system processing all cross-sections. It will further be appreciated that this technique can be applied to the identification of other features (e.g. other objects such as other organs).

However, it will also be appreciated that embodiments of the present disclosure are not limited to this specific method (e.g. a binary search pattern), and other specific techniques for processing the study to output a subset of cross-sections could be used instead (e.g. other predetermined heuristics/methods). Furthermore, it will be appreciated that in some embodiments, in the training phase of the first AI model 112, all cross-sections are processed (though embodiments are not limited to this).

At step S4, the processor 114 obtains the output subset of cross-sections, and inputs a first cross-section from the subset into the second AI model 113. For example, with reference to FIG. 2, the processor 114 could input the first output cross-section 1000+x into the second AI model 113.

At step S5, the second AI model 113 analyses the first cross-section to determine whether the first cross-section includes a lung nodule, and outputs the result. In this sense, as discussed above, the second AI model 113 acts as a known image classifier to analyse the image and output a classification result. Specifics regarding how the second AI model 113 is trained are discussed later with reference to FIGS. 6A and 6B.

At step S6, the processor 114 processes the output from the second AI model 113.

If the output indicates that the first cross-section does not include a lung nodule, and there are still remaining cross-sections output by the first AI model 112 which have not yet been analysed by the second AI model 113, then no conclusion can be drawn regarding whether or not the study includes a lung nodule because a nodule may still be present in a different cross-section.

Therefore, if the output indicates that the first cross-section does not include a lung nodule, the method proceeds to step S7 at which point the processor 114 determines whether or not there are any cross-sections remaining (i.e.

cross-sections which have been output by the first AI model 112 but have not yet been analysed by the second AI model 113).

If the answer at step S7 is yes, the method proceeds to step S8, at which point the processor 113 inputs the next cross-section into the second AI model 113. For example, with reference to FIG. 2, the processor 114 could input the second output cross-section 1000+y.

Steps S5, S6, S7, and S8 are then continually repeated until either the answer at S6 is yes or the answer at S7 is no. If the answer at step S6 is yes, this means that the second AI model 113 has identified a lung nodule, and the processor can conclude that a lung nodule is present in the study. Alternatively, if the answer at step S7 is no, the processor can conclude that all cross-sections which could have included a lung nodule have been analysed and no lung nodules are present. Hence, the processor 114 can conclude that no lung nodules are present in the study.

While FIG. 4 shows that the method ends at step S10, embodiments are not limited to this. For example, in some embodiments the method could then proceed to step S7 to determine whether there are any further lung nodules in the study.

Furthermore, while FIG. 4 shows that the method ends at step S9, embodiments are not limited to this. For example, in some embodiments, the method could then proceed to step S7 and use cross-sections that were discarded (i.e. not output) by the first AI model 112. In this sense, the first AI model 112 would serve the purpose of prioritising the cross-sections considered likely to include the lung nodule, without any risk that the first AI model 112 has discarded a cross-section showing a lung nodule.

With reference to the example of FIG. 3, it can be seen that the study 1000 comprises 100 cross-sections. The first 59 cross-sections do not have any lung tissue. Hence, in this embodiment, these cross-sections would be discarded (i.e. not output) by the first AI model 112 at step S3 of FIG. 4. As a result, the first cross-section to be input to the cross-section model 112 at step S5 would be the $60^{th}$ cross section 1060. However, as can be seen in FIG. 3, the $60^{th}$, $61^{st}$, and $62^{nd}$ cross-section would not show the presence of the lung nodule 22. Hence, steps S5-S8 of FIG. 4 would be repeated until the $63^{rd}$ cross-section 1063 was input at which point the output at step S5 of FIG. 4 would lead to a 'yes' answer at step S6, allowing the processor to determine that a lung nodule is present in the CT study 1000 at step S10.

FIG. 5 shows a comparative flowchart that could be used in a system simply using only a conventional AI classifier (without the use of the first AI model 112). It can be seen that step S1' of FIG. 5 involves receiving the study in the same way as step S1 of FIG. 4.

The method then jumps to step S4' in which the first cross-section is input into the AI classifier. For example, with reference to the example of FIG. 3, this could be the first cross-section 1001.

At step S5', the AI classifier analyses the input cross-section in the same way as step S5 of FIG. 4.

Steps S5' to S8' are then continually repeated to subsequent cross-sections until the answer at step S6' becomes yes, or the answer at step S7' becomes no, in the same way as discussed above with reference to FIG. 5.

It can be seen that for the flowchart of FIG. 5 to reach the determination at step S10' for the example of FIG. 5, this would take 63 iterations of steps S5'-S8'. The vast majority of this time would be spent with the AI classifier (which is trained to classify lung nodules) analysing cross-sections that do not even include any lung tissue.

In contrast, through the use of the first AI model 112, the flowchart of FIG. 4 (corresponding to the operation of the study analyser 110 of this embodiment) takes just 3 iterations of this cycle. It can hence be seen that the inclusion of a first AI model 112 to analyse the study more generally before individual cross-sections are analysed for the identification of a specific feature, results in a significant reduction in wasted time and resources in analysing irrelevant cross-sections. Put differently, by allowing for the application of the second AI model 113 to only a small portion of overall data, this decreases the computational load.

In contrast to a conventional AI architecture (e.g. conventional AI classifier), which can only control its output, the use of the first AI model 112 allows for both the input and the output of the second AI model 113 to be controlled, thereby resulting in superior performance. This is discussed in more detail later.

While the use of a CT study and the identification of lung nodules have been discussed above, as also discussed above, embodiments of the present disclosure are not limited to this. In particular any 3D volume of data including a plurality of cross-section can be used instead, while the study analyser can be configured to identify any suitable predetermined feature.

A further example embodiment will now be discussed with reference to the flow chart of FIG. 6. The study analyser according to this second embodiment is similar to that of the study analyser 110 of the first embodiment, and this discussion will focus on the differences. In particular, in contrast to the first embodiment discussed above which was focused on the identification of lung nodules in CT scans, the study analyser of this second embodiment is focused on identifying whether a brain CT scan was taken with or without a contrast agent.

In the detection of contrast agent in CT brain studies, it is important to determine whether contrast agent is present. However, the presence of contrast agent is generally noticeable only in cross sections containing large blood vessels only (where the presence of the contrast agent is more visible). Other portions of the brain data would be spurious in terms of the task at hand.

Figure 6:
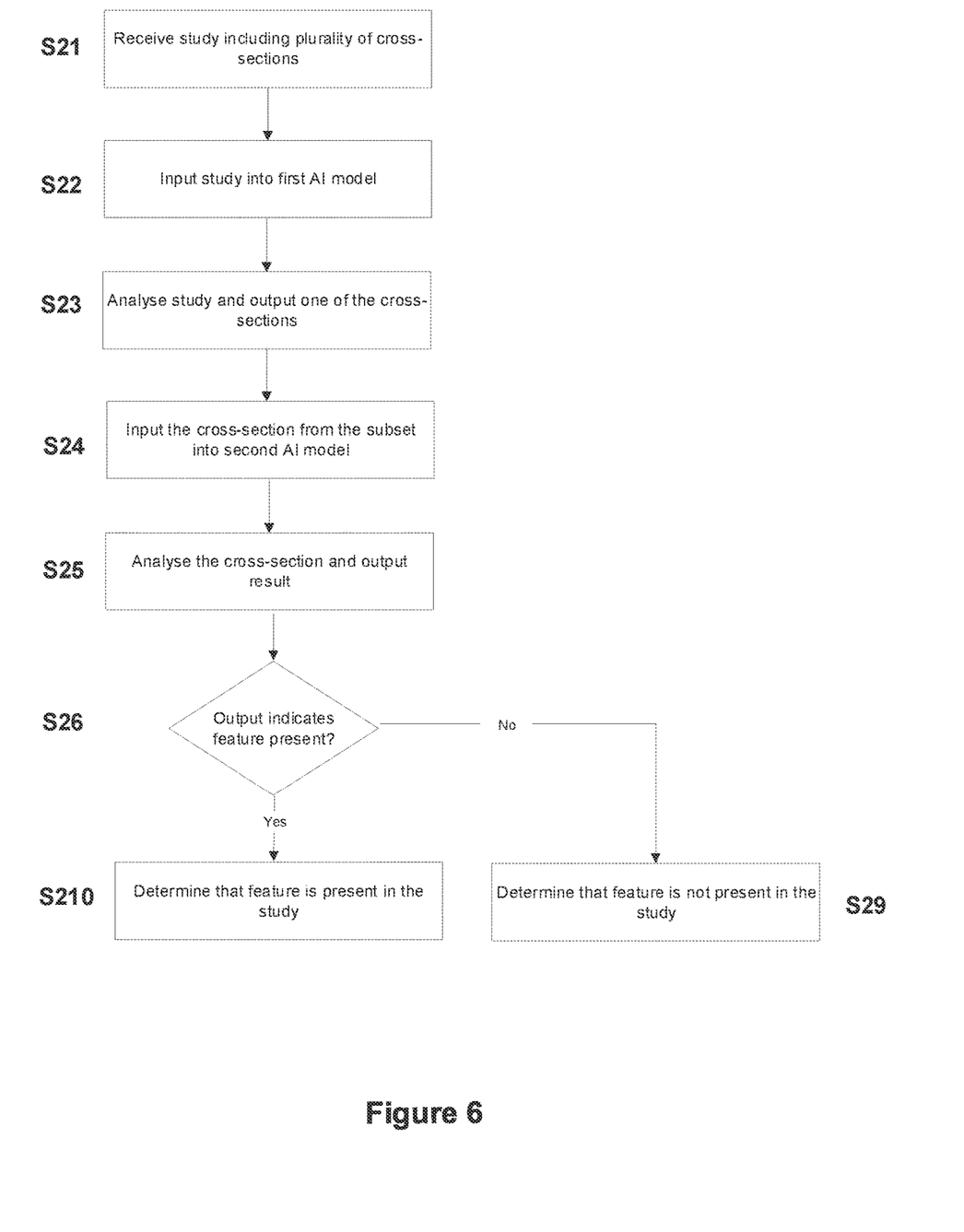
FIG. 6 shows a flowchart of the operation of a study analyser according to an embodiment.

The flow chart of FIG. 6 begins at step S21, in which the study analyser receives the brain CT scan, similarly to step S1.

At step S22, the processor inputs the brain CT scan into the first AI model 112, similarly to step S22.

At step S23, the first AI model 112 analyses the input brain CT scan and outputs a single cross-section. This single cross-section is a cross-section that is identified as having large blood vessels (since this is where the presence of contrast agent would be visible if used in the study).

In this embodiment, the first AI model 112 begins by processing a first (e.g. middle) cross-section of the input study. If this shows large blood vessels (i.e. a blood vessels above a predetermined size), the first AI model 112 stops, and the method proceedings to step S24. If this first cross-section does not show large blood vessels, the first AI model 112 processes a second cross-section from a different part of the study (e.g. halfway between the middle and the bottom), the first AI model 112 stops, and the method proceedings to step S24. Alternatively, if this second cross-section does not show large blood vessels, the first AI model 112 processes another cross-section, and so on.

In this way, the first AI model 112 only needs to process a small number of cross-sections (sometimes only one) in the study in order to identify a cross-section capable of showing the presence of contrast agent (since it includes large blood vessels), thereby reducing the time needed to process the study compared to a system processing all cross-sections. It will further be appreciated that this technique can be applied to the identification of other features.

However, it will also be appreciated that embodiments of the present disclosure are not limited to this specific method (e.g. a binary search pattern), and other specific techniques for processing the study to output a subset of cross-sections could be used instead (e.g. other predetermined heuristics/methods). Furthermore, it will be appreciated that in some embodiments, in the training phase of the first AI model 112, all cross-sections can be processed.

At step S24, the processor then inputs the output cross section into the second AI model 113.

At step S25, the second AI model 113 analyses the input cross-section and outputs a classification result indicating whether or not the cross-section shows the presence of a contrast agent. In this embodiment, the second AI model 113 has been trained similarly to the second AI model 113 of the first embodiment, but with the different focus of detecting the presence of contrast agent in cross-sections.

At step S26, the processor processes the output. If the output indicates that contrast agent is present, the processor proceeds to step S210 in which it determines that contrast agent was used in the study. If the output indicates that contrast agent is not present, the processor determines that contrast agent was not used in the study.

In contrast to the embodiment of FIG. 4, in this case there is no need for the second AI model 113 to analyse multiple cross-sections. This is because if a cross-section having large blood vessels does not show the presence of contrast, it can be concluded that the entire study does not show contrast.

If the first AI model 112 was not used, and only a second AI model (e.g. only a conventional classifier) was used instead (as in the flow chart of FIG. 5), it would be necessary for many individual cross-sections to be individually analysed by the classifier and determined not to show contrast before it could be concluded that the study was taken without contrast. This is because many cross-sections (such as those having small blood vessels) would not show the presence of contrast, even if it was present even if it was used. As a result, the lack of contrast agent in those cross-sections would not allow for the conclusion that the study was taken without contrast.

Hence, the use of the first AI model 112 significantly reduces the amount of wasted time and computational resources that would be spent by a conventional classifier analysing irrelevant cross-sections.

While the above method has been discussed in relation to brain CT scans, embodiments are not limited to this. It will be appreciated that this method can also be used for many other types of study. Furthermore, it will be appreciate that the method of FIG. 4 (including the first AI model 112 outputting more than one cross-section, and the numerous iterations of steps S5-S8) could be used instead. For example, by having the second AI model 113 analyse multiple cross-sections, this could increase confidence in the resulting determination, even for the detection of contrast agent in brain CT scans.

Figure 7:
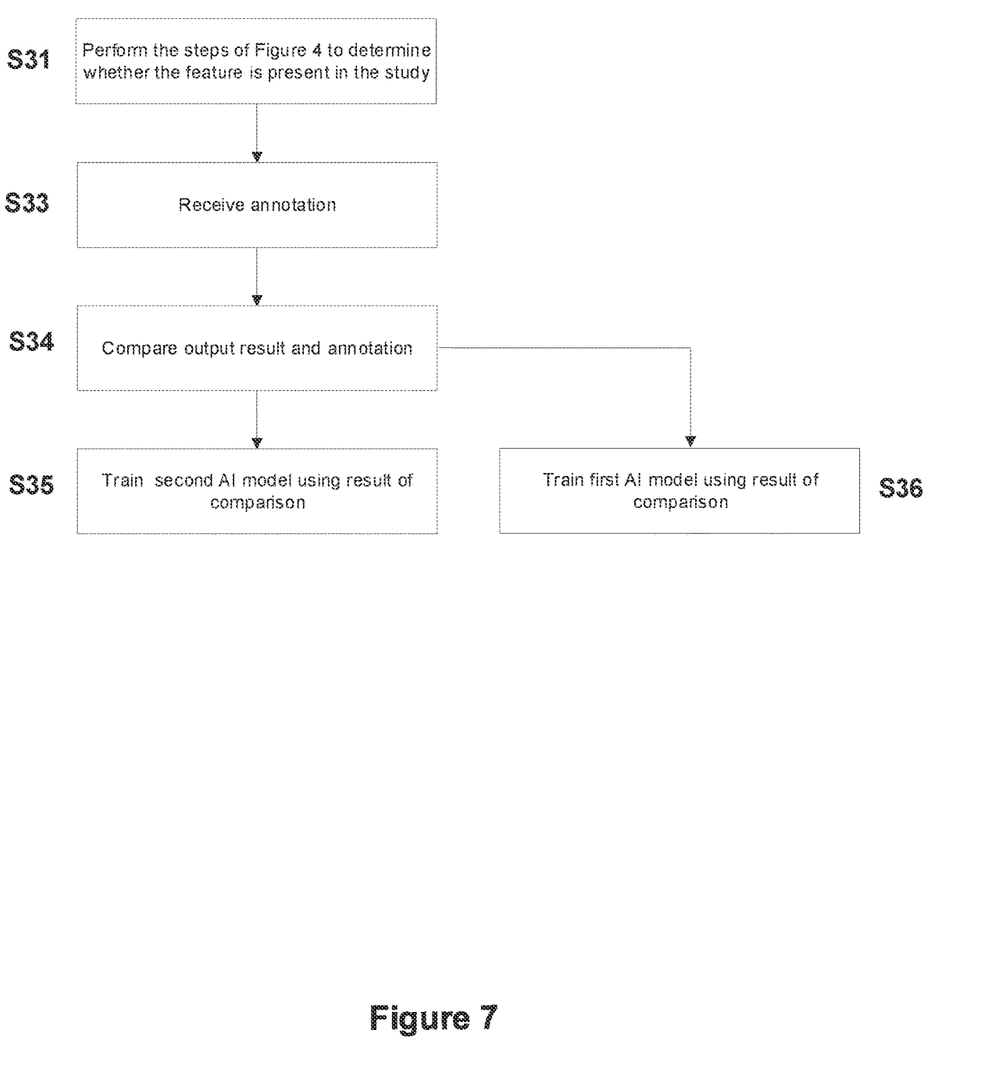
FIG. 7 shows a flow chart of the training of the AI models in the system of FIG. 1.

FIG. 7 shows a flow chart showing how the first AI model 112 and the second AI model 113 of the first embodiment are trained.

FIG. 7 begins at step S31 by performing the steps of FIG. 4. As discussed above, the flow chart of FIG. 4 ends with either a determination that the feature (e.g. lung nodule) is present in the study, or that it is not present in the study.

At step S33, the communication interface 111 receives an annotation of the study. In this embodiment, the annotation is a 'weak annotation' simply indicating whether or not the study includes the feature (e.g. the lung nodule), and does not include any specific information regarding individual cross-sections, or where the lung nodule is present in the study. However, embodiments are not limited to this, and any suitable annotation, such as bounding boxes or segmentation could be used instead. In addition, annotation of individual cross-sections can be used in embodiments.

Furthermore, while step S33 is shown as a separate step in FIG. 7, embodiments are not limited to this. For example, in some embodiments, the annotation could be received at the same time as the study (i.e. at step S1 of FIG. 4).

At step S34, the processor 114 compares the annotation and the determination from the study analyser 110 of whether or not the study includes the predetermined feature (e.g. lung nodule). In other words, the processor 114 determines whether or not the study analyser 110 has correctly classified the input study.

At step S35, the processor then feeds back the result of this comparison to the second AI model 113. In addition, at step S36, this feedback is also provided to the first AI model 112.

Based on this feedback, the second AI model 113 trains to better recognise the predetermined feature (e.g. lung nodules) in cross-sections, while the first AI model 112 trains to output the cross-sections capable of including the predetermined feature from an input study. For example, in the context of the predetermined feature being a lung nodule, the first AI model 112 could train to better recognise which cross-sections represent the lungs, based on patterns of cross-sections in the study.

In more detail, as with known neural networks, the second AI model 113 (which is a neural network in this embodiment) attempts to adjust its weights so as to minimize its cost function. The first AI model 112 (which is also a neural network in this embodiment) also aims to minimise its cost function, but does this by discarding part of the input data (i.e. only outputting some of the input cross-sections). Hence, both AI models aim to reduce the cost function, but the second AI model 113 does that by assigning probabilities to the individual pixels (as do know classifiers), while the first AI model 112 does this by assigning in/out decisions for entire cross-sections.

In this embodiment, the first AI model 112 and the second AI model 113 are both trained using backpropagation. In a variant of this embodiment, the backpropagation is combined with stochastic gradient descent. However, embodiments are not limited to this, and it will be appreciated that any suitable training algorithms could be used for either models. For example, any of the Inception, AlexNet, or VGG16 frameworks could be used to train the second AI model 113 to perform classification.

In this embodiment, the neural networks are convolutional neural networks. However, embodiments are not limited to this and it will be appreciated that other embodiments could be implemented with other suitable machine learning models. Examples include support vector machines, logistic regression, Naïve Bayes, decision tree learning (e.g. C4.5 algorithm, multivariate adaptive regression splines (MARS), and reinforcement learning.

In this embodiment, the first AI model 112 is limited to discarding a maximum of half of the cross-sections in the study. In other words, the first AI model 112 is required to output at least half of the input cross-sections. By including this limitation, this prevents the first AI model 112 from converging to the trivial "solution", where all of the input cross-sections are discarded, since if no cross-sections are input to the second AI model 113, there can be no errors. However, embodiments are not limited to this example of requiring half of the cross-sections to be output, and such limitations can be driven by the implicit model of the target area.

For example, as discussed above in relation to FIG. 6, in an embodiment in which the overall aim of the study analyser is to identify the presence of contrast agent in brain CT scans, it can be sufficient for the study cross-section to output only one cross-section for subsequent input to the second AI model 113. This is because in this particular example, a conclusion can be drawn based on a single cross-section, provided that cross-section includes large blood vessels, as already discussed above.

Hence, in some embodiments, the first AI model 112 can be limited to only outputting a predetermined number of cross-sections for subsequent input to the second AI model 113. In some examples relating to detecting contrast in brain CT scan, this predetermined number can be one. This saves time (both from the computational point of view and for the reviewing by physician), since the study analyser can make a decision on whether contrast agent is included in the study based on one or very few cross-sections.

There are a number of possible strategies for applying this limitation in different embodiments. Examples include that the first AI model 112 would be allowed to remove a certain predetermined percentage of the cross sections in each study, such as the example of 50% (i.e. half) discussed above. Another example is that the first AI model 112 would be allowed to accept certain contiguous part of the study (e.g. representing the lungs). Yet another example is that the first AI model 112 would be allowed to accept certain predetermined number of contiguous segments in the study having a combined length of at least a predetermined threshold.

In other embodiments, no such limitation is required. For example, instead of this limitation regarding the number of cross-sections to be output, the study analyser could instead treat a study for which the first AI model 112 outputs zero cross-sections as an incorrect analysis result. In other words, instead of comparing an output from the second AI model 113 with an annotation to determine whether the output is correct or incorrect, the processor could simply treat the (non-existent) output for the study as being incorrect, and feedback to the first AI model 112 that the result was incorrect. This would prevent the first AI model 112 from converging to the trivial "solution", where all the input cross-sections are discarded, since if no cross-sections are input to the second AI model 113, there would be an error (i.e. feedback that it was incorrect). Through this method, the first AI model 112 would be prevented from outputting zero cross-sections, without any limitation being required on a specific number of cross-sections to output.

Figure 8A:
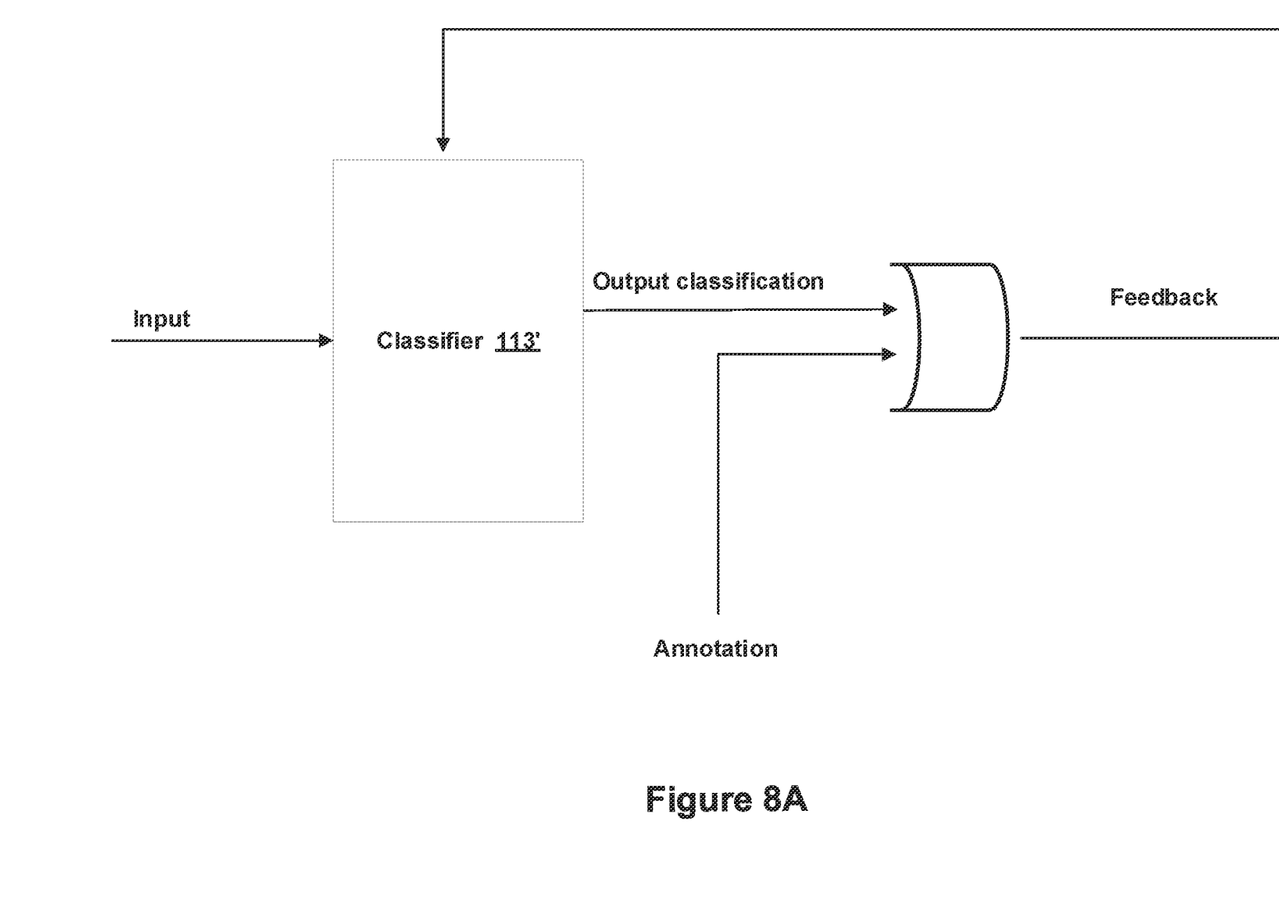
FIG. 8A shows a circuit representing the flow of data in a system that could be implemented using conventional techniques.

The benefits provided by the method of training discussed above are usefully illustrated by FIGS. 8A and 8B. FIG. 8A shows a circuit representing the flow of data in a system that could be implemented using conventional techniques. FIG. 8B shows a circuit representing the flow of data in the flow chart of FIG. 7 during the training phase.

It can be seen in FIG. 8A that the input training data goes into a conventional classifier 113' (one cross-sections at a time) and that the classifier then outputs a classification. With reference to FIG. 5 discussed above, this could involve multiple cross-sections from a study being sequentially input until a determination for the study is made (e.g. a determination that there is a lung nodule present or that there is not a lung nodule present). The annotation is then fed in and compared with the result obtained from the classifier. The result of this comparison is then fed back to the classifier 113'.

Figure 8B:
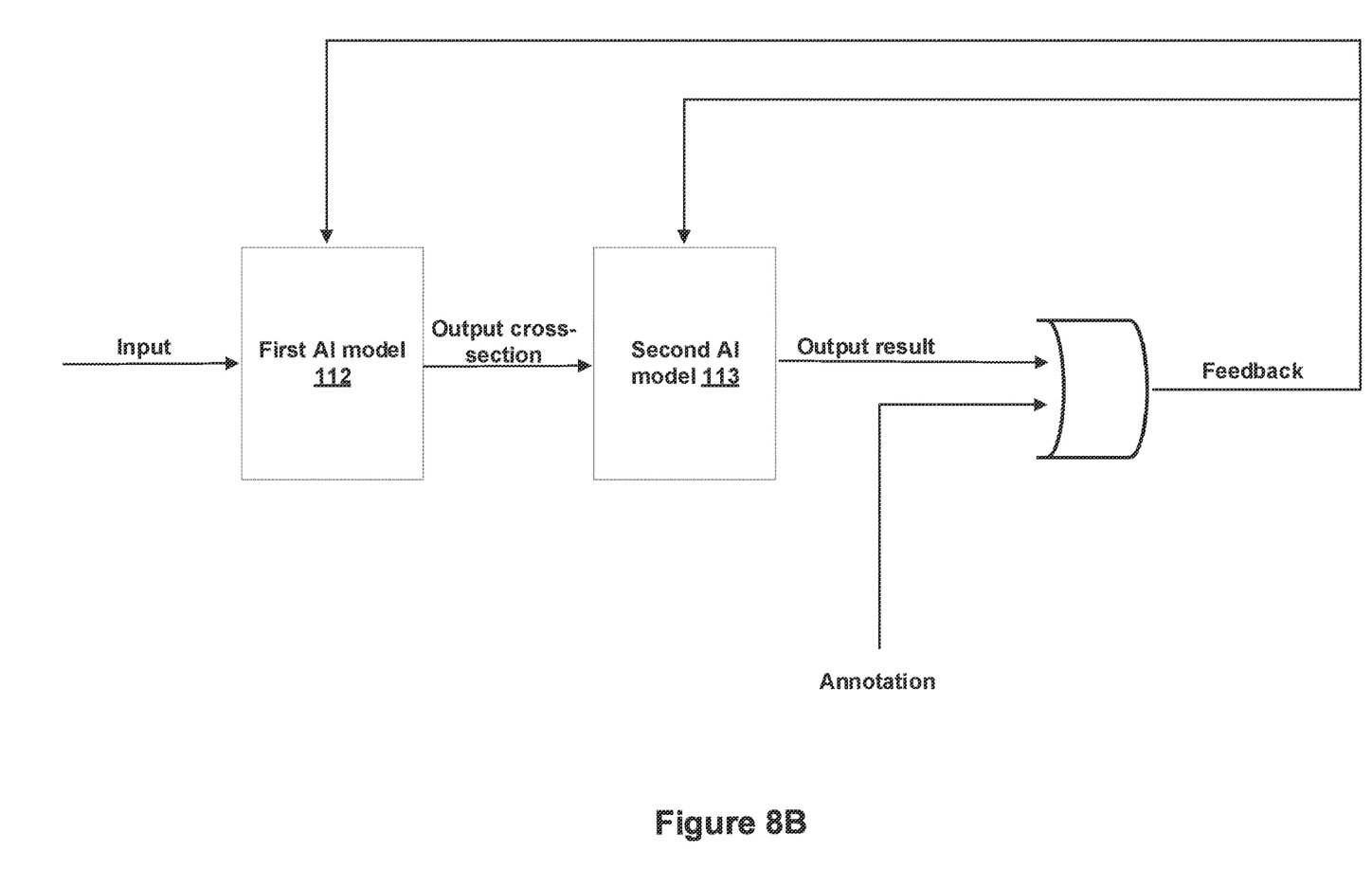
FIG. 8B shows a circuit representing the flow of data in the flow chart of FIG. 7 during a training phase.

It can be seen in FIG. 8B that the entire input training data (i.e. a whole study) is input to the first AI model 112. A cross-section from the first AI model 112 is then output to the second AI model 113 for classification. With reference to FIG. 4 discussed above, this could involve multiple cross-sections from a study being sequentially input until a determination for the study is made (e.g. a determination that there is a lung nodule present or that there is not a lung nodule present). The annotation is then fed in and compared with the result obtained from the classifier. The result of this comparison is then fed back to the classifier 113'. In addition, this result is fed back to the first AI model 112.

Hence, in addition to the benefits provided by the first AI model 112 in normal operation (i.e. after training), it can be seen from FIGS. 7, 8A and 8B that the first AI model 112 is also beneficial in the training phase. By initially using a first AI model 112 to filter out some cross-sections, this ensures that more relevant cross-sections are provided to the second AI model 113 for its training. In other words, in the context of identifying lung nodules, by including the first AI model 112 before the second AI model 113, a higher proportion of cross-sections showing lung tissue would be passed on to the second AI model 113 (since the first AI model 112 would be training to discard the non-lung cross-sections).

It might be considered that one possible approach to the problems addressed by the embodiments discussed above would be to split the classification process into two stages. First, the area of interest (e.g. correct organ or correct part of the organ) is identified (by applying a lung classifier sequentially to individual cross-sections). Then, the specific feature (e.g. lung nodule) is identified in the second classification stage (by using a nodule classifier). However, in order to apply this approach, it would be necessary to get a "truth file" for the first stage. In other words, it would require human experts that would manually determine areas of interest in the training set. At best, this would be a laborious process (e.g. one would have to provide precise 3D delineation of the lungs or kidney etc.). At worst it would be almost impossible (e.g. it is difficult even for human experts to determine which areas of the brain are suitable for the contrast agent detection).

In contrast, as can be seen in FIGS. 7 and 8B, the inclusion of the first AI model 112 does not require any additional annotation to be performed. In particular, the same annotation and feedback which would already be provided for the second AI model 113 in a conventional system (e.g. with a conventional classifier) can also be provided to the first AI model 112 for training.

It will be appreciated that many variants can be applied to the embodiments discussed above. For example, the method for regularization of the studies so that system will provide uniform performance both for short studies (say having 50 cross-sections or less) and large studies having over 300 cross-sections can be changed. For example, based on metadata of the study, the study analyser 110 can determine that the scan is a full body scan. As a result, the study analyser 110 can determine, for example for lung nodule detection, that a large proportion of the study must be discarded. Alternatively, if the metadata indicates that the scan is only lung scan, a small number (or zero) cross-sections would need to be determined.

As another example, the method for application of the second AI model 113 can also be varied. For example, any known classification techniques could be used, some of which have already been discussed above.

While the present disclosure has generally been discussed in relation to CT studies, embodiments are not limited to this and the study can be any 3D volume of a data comprising a plurality of cross-sectional images. Examples include other medical studies (e.g. MRI) as well as non-medical studies. Furthermore, while the present disclosure has generally been discussed in relation to horizontal cross-sections, different directions can be used. For example, while typically CT (or MRI) studies are organized in the form of horizontal cross-sections, a similar approach can be applied to vertical slices (a sagittal view), further limiting the area of interest from both right-left and back-front (or even up-down) directions. For example, for studies of the kidney, good organ delineation can be obtained using left-right and back-front planes, as well As discussed, embodiments provide systems and method for determining whether a dataset comprising a plurality of cross-sectional images includes a predetermined feature. These systems and methods involve the use of a first AI model to analyse the dataset to identify a subset of cross-sectional images representing a portion of the dataset capable of including the predetermined feature.

This first AI model essentially filters the cross-sectional images in the dataset, and only outputs relevant cross-sections for analysis by a second AI model (e.g. a classification unit). For example, if the objective of the system is to identify lung nodules in a CT scan, the first AI model could act to exclude cross-sectional images that do not represent the lung, while outputting cross-sectional images which do represent the lung to the second AI model. This reduces the time and processing power required by the second AI model, which could otherwise be spent analysing irrelevant cross-sectional images (e.g. images that do not even include any lung tissue).

In other words, the inclusion of a first AI model to analyse the study more generally before individual cross-sections are analysed for the presence of a specific feature (such as a lesion or the presence of brain contrast), results in a significant reduction in wasted time and resources in analysing irrelevant cross-sections. By allowing for the application of the second AI model 113 to only a small portion of overall data, this decreases the computational load.

In contrast to a conventional AI architecture (e.g. conventional AI classifier), which can only control its output, the use of the first AI model 112 allows for both the input and the output of the second AI model 113 to be controlled, thereby resulting in superior performance.

In some embodiments, the second AI model 113 is not even required to analyse multiple cross-sections. For example, if the objective of the system is to identify whether contrast agent was used in a brain CT scan, if a cross-section having large blood vessels does not show the presence of contrast, it can be concluded that the entire study does not show contrast. In this example if only a second AI model (e.g. only a conventional classifier) was used instead it would be necessary for many individual cross-sections to be individually analysed by the classifier and determined not to show contrast before it could be concluded that the study was taken without contrast. This is because many cross-sections (such as those having small blood vessels) would not show the presence of contrast, even if it was present even if it was used. As a result, the lack of contrast agent in those cross-sections would not allow for the conclusion that the study was taken without contrast. Hence, the use of the first AI model 112 significantly reduces the amount of wasted time and computational resources that would be spent by a conventional classifier analysing irrelevant cross-sections.

In relation to training, by initially using a first AI model to filter out some cross-sections, it can be ensured that more relevant cross-sections are provided to the second AI model for training. For example, in the example context of identifying lung nodules, by including the first AI model before the second AI model, a higher proportion of cross-sections showing lung tissue would be passed on to the second AI model (since the first AI model would be training to discard the non-lung cross-sections).

As discussed above, it might be considered that one possible approach to the problems addressed by the embodiments discussed above would be to split the classification process into two stages. First, the area of interest (e.g. correct organ or correct part of the organ) is identified (by applying a lung classifier sequentially to individual cross-sections). Then, the specific feature (e.g. lung nodule) is identified in the second classification stage (by using a nodule classifier). However, in order to apply this approach, it would be necessary to get a "truth file" for the first stage. In other words, it would require human experts that would manually determine areas of interest in the training set. At best, this would be a laborious process (e.g. one would have to provide precise 3D delineation of the lungs or kidney etc.). At worst it would be almost impossible (e.g. it is difficult even for human experts to determine which areas of the brain are suitable for the contrast agent detection).

In contrast, the inclusion of the first AI model in embodiments of the present disclosure does not require any additional annotation to be performed. In particular, the same annotation and feedback which would already be provided for the second AI model 113 in a conventional system (e.g. with a conventional classifier) can also be provided to the first AI model 112 for training.

Embodiments can provide a computer a non-transitory computer readable medium storing software comprising instructions executable by one or more computers which, upon such executions, causes the one or more computers to perform the method of embodiments.

Examples of computer-readable media include both volatile and non-volatile media, removable and non-removable media, and include, but are not limited to: solid state memories; removable disks; hard disk drives; magnetic media; and optical disks. In general, the computer-readable media include any type of medium suitable for storing, encoding, or carrying a series of instructions executable by one or more computers to perform any one or more of the processes and features described herein.

The apparatuses described above may be implemented on a single device or multiple devices in communication. More generally, it will be appreciated that the hardware used by embodiments can take a number of different forms. For example, the components of embodiments could be provided by a single device, or different components of could be provided on separate devices. More generally, it will be appreciated that embodiments can provide a system that comprises one device or several devices in communication.

Although some embodiments are described above in which the internet is used, this is not essential. Embodiments can be applied to an application shared between machines that communicate with each other, for example, over a network. Therefore, although the specific embodiment network uses the Internet, embodiments are applicable to any network whether it be a conventional landline network or a wireless network. More specifically, embodiments of the present present disclosure are applicable to the Internet, an intranet, an extranet, a local area network, a wide area network or a network employing wireless application protocol.

Many further variations and modifications will suggest themselves to those versed in the art upon making reference to the foregoing illustrative embodiments, which are given by way of example only, and which are not intended to limit the scope of the disclosed embodiments, that being determined by the appended claims.

The invention claimed is:

1. A system for determining whether a dataset comprising a plurality of cross-sectional images includes a predetermined feature, the system comprising:
   a first AI model configured to:
      receive a dataset comprising a plurality of cross-sectional images as an input,
      analyse the dataset to identify a subset of cross-sectional images of the dataset capable of including the predetermined feature, and
      output the subset;
   a second AI model configured to:
      receive a first cross-sectional image from the subset,
      analyse the first cross-sectional image to determine whether the first cross-sectional image includes the predetermined feature, and
      output an indication of whether the first cross-sectional image includes the predetermined feature; and
   a processor configured to:
      provide the dataset as an input to the first AI model,
      obtain the output subset from the first AI model,
      provide the first cross-sectional image from the subset as an input to the second AI model, obtain the output from the second AI model, and
      when the output from the second AI model indicates that the first cross-sectional image includes the pre-determined feature, the processor is configured to determine that the dataset includes the predetermined feature, wherein the dataset is a brain CT study, and the pre-determined feature is the presence of contrast agent.

2. The system of claim 1, wherein the subset comprises only one cross-sectional image.

3. The system of claim 1, wherein the subset comprises a contiguous plurality of cross-sectional images.

4. The system of claim 1, wherein the first AI model is configured to output at least a predetermined proportion of the cross-sectional images from the dataset in the subset.

5. The system of claim 1, further comprising that when the output from the second AI model indicates that the first cross-sectional image does not include the pre-determined feature, the processor is configured to determine that the dataset does not include the predetermined feature.

6. The system of claim 1, further comprising that when the output from the second AI model indicates that the first cross-sectional image does not include the pre-determined feature, the processor is configured to:
   provide a second cross-sectional image from the subset as an input to the second AI model,
   obtain an output from the second AI model for the second cross-section, and
   when the output from the second AI model indicates that the second cross-sectional image includes the pre-determined feature, determine that the dataset includes the predetermined feature.

7. The system of claim 6, further comprising that when outputs from the second AI model indicate that none of the cross-sectional images include the pre-determined feature, the processor is configured to determine that the dataset does not include the predetermined feature.

8. The system of claim 1, wherein the second AI model is a classification model.

9. A computer implemented method for determining whether a dataset comprising a plurality of cross-sectional images includes a predetermined feature, the method comprising:
   inputting, by a processor, dataset comprising a plurality of cross-sectional images into a first AI model,
   analysing, by the first AI model, the dataset to identify a subset of cross-sectional images of the dataset capable of including the predetermined feature, and
   outputting, by the first AI model, the subset;
   inputting, by the processor, a first cross-sectional image from the subset into a second AI model,
   analysing, by the second AI model, the first cross-sectional image to determine whether the first cross-sectional image includes the predetermined feature, and
   outputting, by the second AI model, an indication of whether the first cross-sectional image includes the predetermined feature; and
   when the output of the second AI model indicates that the first cross-sectional image includes the pre-determined feature, determining, by the processor, that the dataset includes the predetermined feature, wherein the dataset is a brain CT study, and the pre-determined feature is the presence of contrast agent.

10. A system for training a first AI model to identify a subset of a plurality of cross-sectional images in a dataset that are capable of including a predetermined feature and training a second AI model to determine whether cross-section image includes a predetermined feature, the system comprising:
   a first AI model to:
      receive dataset comprising a plurality of cross-sectional images as an input,
      analyse the dataset to identify a subset of cross-sectional images of the dataset capable of including the predetermined feature, and
      output the subset;
   a second AI model to:
      receive a first cross-sectional image from the subset,
      analyse the first cross-sectional image to determine whether the first cross-sectional image includes the predetermined feature, and
      output an indication of whether the first cross-sectional image includes the predetermined feature;
   an annotation unit to obtain an annotation indicating whether the predetermined feature is in the dataset; and
   a processor configured to:
      provide the dataset as an input to the first AI model,
      provide the first cross-sectional image from the subset as an input to the second AI model, and
      compare the output from the second AI model and the annotation, and
      provide the result of the comparison as feedback to the second AI model to train the second AI model to determine whether a cross-sectional image includes the predetermined feature, and
      provide the result of the comparison as feedback to the first AI model to train the first AI model to identify a subset of a plurality of cross-sectional images in a dataset that are capable of including the predetermined feature.

11. The system of claim 10, wherein the annotation indicates whether the predetermined feature is in the first cross-sectional image.

12. A computer implemented method for training a first AI model to identify a subset of a plurality of cross-sectional images in a dataset that are capable of including a predetermined feature and training a second AI model to determine whether a cross-sectional image includes a predetermined feature, the method comprising:
   inputting, by a processor, dataset comprising a plurality of cross-sectional images into a first AI model,
   analyse the dataset to identify a subset of cross-sectional images of the dataset capable of including the predetermined feature, and
   outputting, by the first AI model, the subset;
   inputting, by the processor, a first cross-sectional image from the subset into a second AI model,
   analysing, by the second AI model, the first cross-sectional image to determine whether the first cross-sectional image includes the predetermined feature, and
   outputting, by the second AI model, an indication of whether the first cross-sectional image includes the predetermined feature; and
   obtaining, by an annotation unit, an annotation indicating whether the predetermined feature is in the dataset;
   comparing, by the processor, the output from the second AI model and the annotation; and
   providing, by the processor, the result of the comparison as feedback to the second AI model to train the second AI model to determine whether a cross-sectional image includes the predetermined feature; and
   providing, by the processor, the result of the comparison as feedback to the first AI model to train the first AI model to identify a subset of a plurality of cross-sectional images in a dataset that are capable of including the predetermined feature.

13. A non-transitory computer-readable medium having computer-executable instructions configured to cause one or more processors of a computing device to carry out the method of claim 9.

* * * * *